(12) United States Patent
Kwon

(10) Patent No.: US 7,803,112 B2
(45) Date of Patent: *Sep. 28, 2010

(54) APPARATUS AND METHOD FOR DISPLAYING SECTIONAL PLANES OF TARGET OBJECT UTILIZING 3-DIMENSIONAL ULTRASOUND DATA

(75) Inventor: Eui Chul Kwon, Seoul (KR)

(73) Assignee: Medison Co., Ltd., Hongchum-gun (KR)

( * ) Notice: Subject to any disclaimer, the term of this patent is extended or adjusted under 35 U.S.C. 154(b) by 959 days.

This patent is subject to a terminal disclaimer.

(21) Appl. No.: 11/006,609

(22) Filed: Dec. 8, 2004

(65) Prior Publication Data

US 2005/0187474 A1 Aug. 25, 2005

(30) Foreign Application Priority Data

Dec. 31, 2003 (KR) ............ 10-2003-0101188
Nov. 11, 2004 (KR) ............ 10-2004-0091704

(51) Int. Cl.
*A61B 8/00* (2006.01)
(52) U.S. Cl. ...................................... 600/443
(58) Field of Classification Search ............. 600/437, 600/443; 128/916; 382/128, 276, 278, 293; 345/418, 419
See application file for complete search history.

(56) References Cited

U.S. PATENT DOCUMENTS

| 5,396,890 A | 3/1995 | Weng |
| 6,139,498 A | 10/2000 | Katsman et al. |
| RE37,088 E * | 3/2001 | Olstad et al. ............ 600/440 |
| 6,374,674 B1 | 4/2002 | Mine |
| 6,607,488 B1 | 8/2003 | Jackson et al. |
| 6,798,907 B1 * | 9/2004 | Clary et al. ............ 382/187 |

(Continued)

FOREIGN PATENT DOCUMENTS

EP 0 806 682 11/1997

(Continued)

OTHER PUBLICATIONS

Georgios Sakas, et al., "Interactive Visualization of Large Scalar Voxel Fields", Proceedings of the Visualization Conferences, vol. CONF. 3, XP-010029602, Oct. 19, 1992, pp. 29-36.
Richard A. Robb, et al., "Three-Dimensional Visualization in Medicine and Biology", Book Chapter in: Handbook of Medical Imaging, Processing and Analysis, XP-002270429, Sep. 1, 2000, pp. 1-43.

(Continued)

*Primary Examiner*—Brian Casler
*Assistant Examiner*—Elmer Chao
(74) *Attorney, Agent, or Firm*—Oblon, Spivak, McClelland, Maier & Neustadt, L.L.P.

(57) ABSTRACT

An apparatus for displaying sectional planes of a target object utilizing 3 dimensional (3D) ultrasound data. The apparatus is capable of scanning the target object in real time by improving a scan conversion speed and virtually scans the target object by storing previously acquired 3D data. The apparatus, which displays a target object by using 3D ultrasound data, includes 1) a scan conversion unit for performing scan conversion to convert Cartesian coordinates for display on a screen of a display device to conical coordinates of 3D data, and 2) a rendering unit for rendering multiple sectional plane images, based on the 3D scan conversion, parallel with a reference sectional plane.

13 Claims, 22 Drawing Sheets
(4 of 22 Drawing Sheet(s) Filed in Color)

U.S. PATENT DOCUMENTS

| | | | |
|---|---|---|---|
| 7,087,022 B2 * | 8/2006 | Chalana et al. | 600/449 |
| 7,436,402 B2 * | 10/2008 | Kwon et al. | 345/419 |
| 2004/0138560 A1 * | 7/2004 | Paladini | 600/437 |
| 2004/0186369 A1 * | 9/2004 | Lam | 600/407 |
| 2006/0100512 A1 * | 5/2006 | Lee | 600/437 |

FOREIGN PATENT DOCUMENTS

| | | |
|---|---|---|
| EP | 1 046 929 | 10/2000 |

OTHER PUBLICATIONS

Svetoslav Ivanov Nikolov, et al., "Real Time 3D Visualization of ultrasonic data using a standard PC", Ultrasonics, IPC Science and Technology Press Ltd., vol. 41, No. 6, XP-004437390, Aug. 2003, pp. 421-426.

Kevin Kreeger, et al., "Mixing Translucent Polygons with Volumes", Visualization '99, XP-010364952, Oct. 24, 1999, pp. 191-198,525.

* cited by examiner

A sectional plane

B sectional plane

C sectional plane

Sectional plane drawing strait line on A sectional plane

Sectional plane drawing strait line on B sectional plane

Sectional plane drawing curved line on C sectional plane

Sectional plane drawing curved line on A sectional plane

APPARATUS AND METHOD FOR DISPLAYING SECTIONAL PLANES OF TARGET OBJECT UTILIZING 3-DIMENSIONAL ULTRASOUND DATA

The present invention relates to an apparatus and method for displaying sectional planes of a target object utilizing 3-dimensional (3D) ultrasound data. More particularly, the present invention relates to an apparatus and method for displaying sectional planes of a target object utilizing 3D ultrasound data in order to display the target object in real time.

BACKGROUND OF THE INVENTION

Generally, in a system utilizing 3-dimensional (3D) ultrasound data, a 3D ultrasound diagnostic device acquires the 3D ultrasound data of a target object by using a probe. The 3D ultrasound diagnostic device then displays a 3D image of the target object on a screen of a display device by converting conical coordinates of the acquired data to Cartesian coordinates suitable for display (scan conversion). An Image area of the target object displayed on the screen of a display device through the scan conversion and rendering is called a "view." An example of the view is illustrated in FIG. 1. The view 101 includes: a 3D ultrasound image 102 of the target object; a 2D ultrasound image 103 for an A sectional plane representing a front side of the 3D ultrasound image 103; a 2D ultrasound image 104 for a B sectional plane representing a lateral side of the 3D ultrasound image 103; and a 2D ultrasound image 105 for a C sectional plane representing a top side of the 3D ultrasound image 102.

FIGS. 2A to 2C show the A, B and C sectional planes in a 3D ultrasound image for the target object. A solid line represents the target object and dashed planes represent the A, B and C sectional planes in FIGS. 2A, 2B and 2C, respectively.

However, the conventional 3D ultrasound diagnostic device mentioned above has the following problems. First, a problem exists in that it takes a long time for performing the scan conversion of the 3D data in the conventional 3D ultrasound diagnostic device. Since the ultrasound images 102 to 105 are configured with the conical coordinates of 3D data, the scan-conversion for the conical coordinates of the 3D data is required to display the 3D data as a view represented with the Cartesian coordinates of the 3D data. This is because the display region of the display device is based on the Cartesian coordinates. However, an arc tangent operation, which is performed for the scan conversion, requires a long operation time. In addition, whenever locations of the 3D data, which are scan-converted to the Cartesian coordinates for rendering 3D data, are changed due to a 3D view operation, the scan conversion should be performed. This is so that the amount of calculation can be increased. As mentioned above, the conventional 3D ultrasound diagnostic device has the problem in that a prolonged time is required to perform a conversion process of the 3D data in order to obtain a desired type from the 3D data. Second, since the acquired data are not stored as 3D data according to the conventional ultrasound diagnostic device, a problem exists in that the 3D information of the target object should be acquired whenever the target object is diagnosed. For example, the conventional ultrasound diagnostic device directly displays an image of information related to organs of a patient on a monitor or the like. Therefore, the patient can be diagnosed and the condition of the patient can be analyzed only when the patient is present. That is, since the 3D data acquired from the target object are not stored, when the patient is not present, a clinical diagnosis can be performed based on just a past diagnosis picture or calling the patient again later.

Third, there exists a problem in that the conventional 3D ultrasound device does not provide images of the 3D sectional planes (e.g. coronal, sagital or axial plane) that is sufficient for diagnosis. Until now, the 3D ultrasound diagnostic device has been used to satisfy human curiosity rather than for a substantial medical examination of the patient by using the 3D ultrasound data. Namely, the conventional 3D ultrasound diagnostic device has been focused to 3-dimensionally displaying the target object instead of displaying the sectional planes necessary to examine the patient. Even if the conventional 3D ultrasound diagnostic device displays the image of the sectional planes, that image is only for 3D image of the target object and a specific image of the A, B or C sectional plane is merely displayed.

Recently, as the market for the 3D ultrasound diagnostic device has increased and a diagnostic application of the 3D ultrasound image has also increased, it has been required to: more quickly display the 3D data; conveniently display the image of the sectional plane in more detail; and perform an identical operation by using stored data even if a patient does not exist.

SUMMARY OF THE INVENTION

It is an objective of the present invention to provide an apparatus and method for displaying an image of sectional planes of a target object utilizing 3 dimensional (3D) ultrasound data capable of scanning the target object in real time by improving a scan conversion speed and virtually scanning the target object by storing previously acquired 3D data.

In accordance with an aspect of the present invention, there is provided an apparatus displaying a target object by using 3D ultrasound data, including: a scan conversion unit for performing scan conversion to convert conical coordinates of 3D data to Cartesian coordinates for display on a screen of a display device; and a rendering unit for rendering multiple sectional plane images, which are based on the scan-converted 3D data, parallel with a reference sectional plane.

In accordance with another aspect of the present invention, there is provided a method for displaying a target object by using 3D ultrasound data, including the steps of: storing indices matched with Cartesian coordinate of a screen in a display device to display a 3D image of the target object and operation resulting values of operations to convert Cartesian coordinates to conical coordinates coordinate in a geometric look-up table storage unit; receiving reference sectional plane information from an interface device, receiving 3D data of the target object from a probe or a 3D data storage device, and determining whether a current display region displaying an ultrasound image based on the 3D data of the target object is different from a previous display region on the screen; calculating the display region to display the image on the screen when the display region is changed; scan-converting 3D data of the target object by retrieving the operation resulting values from the geometric look-up table storage unit in order to convert Cartesian coordinates to conical coordinates corresponding to the calculated display region; and rendering multiple sectional plane images based on the scan-converted 3D data, wherein the multiple sectional plane images are parallel with a reference sectional plane in a vertical direction to the reference sectional plane.

In accordance with further another aspect of the present invention, there is provided a method for displaying slice images of a target object by using 3D ultrasound data, including the steps of: setting a reference sectional plane of the target object to be displayed; acquiring the 3D ultrasound data of the target object; displaying the reference sectional plane image; drawing a line on the displayed reference sectional plane for displaying a desired oblique sectional plane; and displaying the desired oblique sectional plane perpendicular to the reference sectional plane taken along the line by using an anti-aliasing method.

BRIEF DESCRIPTION OF THE DRAWINGS

The above and other objects and features of the present invention will become apparent from the following description of preferred embodiments given in conjunction with the accompanying drawings, in which.

The patent or application file contains at least one drawing executed in color. Copies of this patent or patent application publication with color drawing(s) will be provided by the Office upon request and payment of the necessary fee.

DETAILED DESCRIPTION OF THE PRESENT INVENTION

I. Real-time Multiple Sectional Plane Images

Figure 3A:
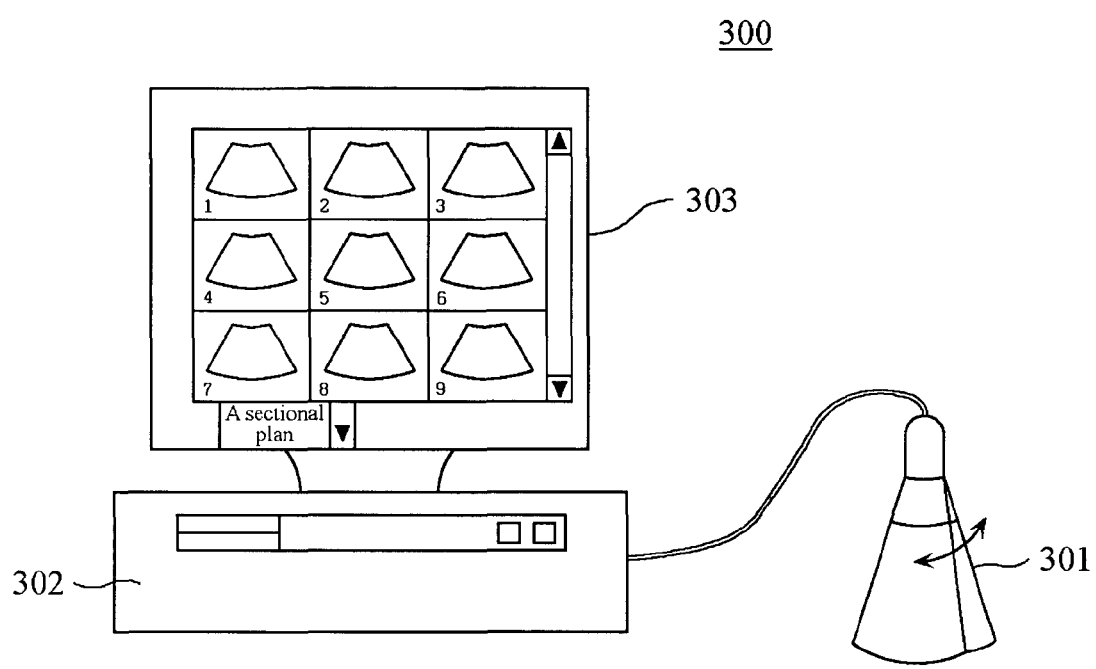
FIG. 3A is a schematic diagram showing a ultrasound diagnostic system in accordance with the present invention.

FIG. 3A is a diagram illustrating a real-time ultrasound diagnostic system 300 in accordance with the preferred embodiment of the present invention.

As illustrated in FIG. 3A, the real-time ultrasound diagnostic system 300 includes a probe 301, a display device 303 and a body 302. The probe 301 is used to acquire 3D data of a target object to be displayed. A mechanical scanning process (scan by moving a mechanical arm or rotating a stepping motor) or a hand-free process (scan by a user's hand) may be applied to the probe 301. The display device 303 (e.g., a monitor) is used to display the data acquired from the probe 301. It should be noted herein that as long as the display device can display a 3D image in accordance with the present invention, any type of display device could be used. The body 302 processes the 3D data acquired from the probe 301 to be displayed on a display region of the display device 303. Then, the data processing is carried out in a rendering device for a 3D ultrasound diagnostic system included in the body 302. Hereinafter, the rendering device for the 3D ultrasound diagnostic system will be described.

Figure 3B:
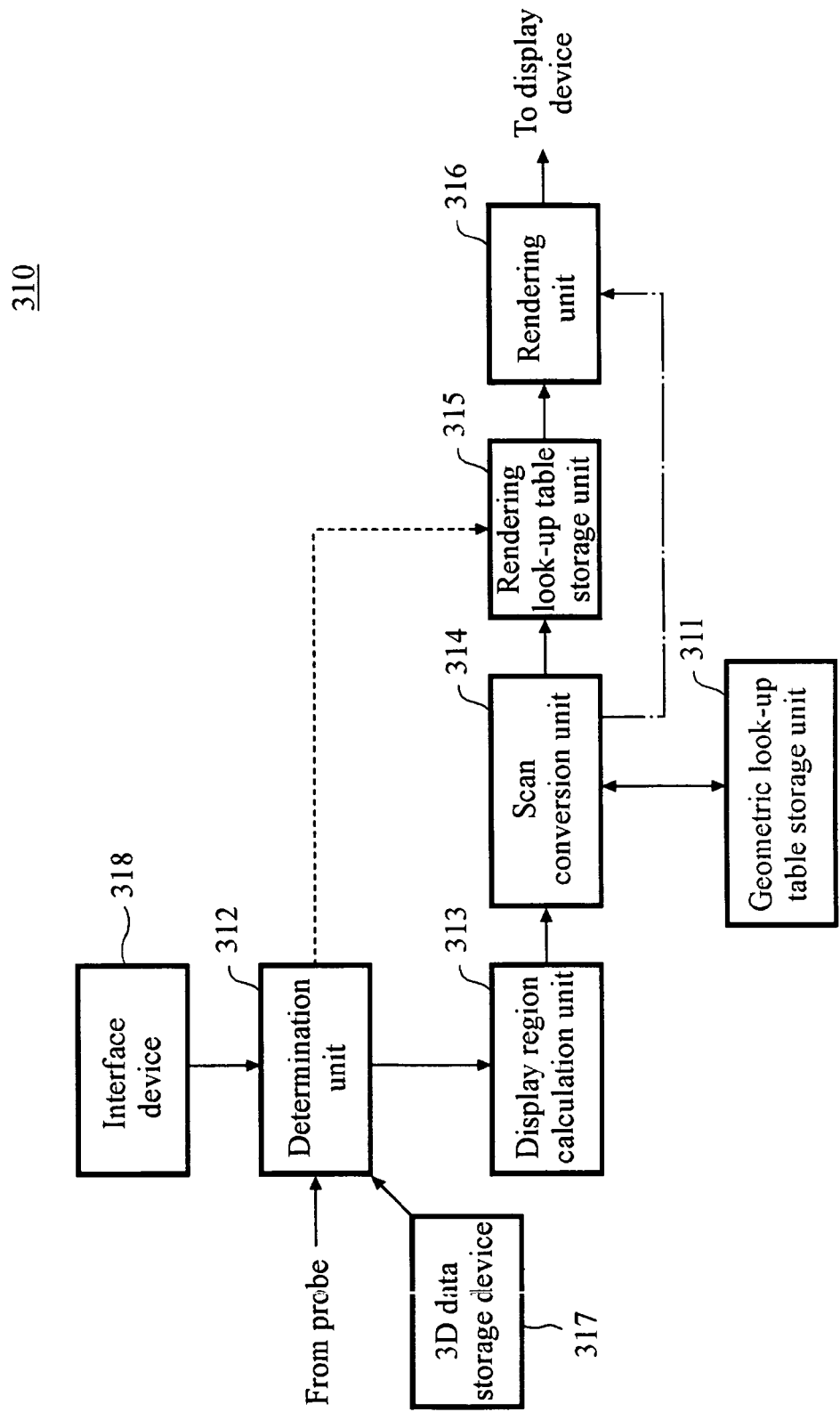
FIG. 3B is a block diagram illustrating a rendering device included in a body of a ultrasound diagnostic system in FIG. 3A in accordance with the present invention.

FIG. 3B is a block diagram illustrating the rendering device 310 for the 3D ultrasound diagnostic system in accordance with the preferred embodiment of the present invention. As illustrated in FIG. 3B, the rendering device 310 for the 3D ultrasound diagnostic system 300 includes an interface device 318, a determination unit 312, a display region calculation unit 131, a scan conversion unit 314, a geometric look-up table storage unit 311, a rendering look-up table storage unit 315, a rendering unit 316 and a data storing device 317.

Each element configuring the rendering device 310 for the real-time 3D ultrasound diagnostic system will be described below in detail.

The interface device 318 receives a view operation command, which is inputted from a user or is automatically set. The view operation command essentially commands how to display and process the 3D data acquired from the probe 301 and then outputs after appropriately converting the commands. The view operation command may include commands related to a reference sectional plane of the target object to be displayed, a screen layout, a display region and the like. The operation of the interface device 318 for the above commands will be described.

The interface device 318 receives the information of a reference sectional plane from the user. It then outputs a command so that a plurality of sectional planes of the target object parallel with the reference sectional plane is displayed in a vertical direction to the reference sectional plane The reference sectional plane is selectively determined from one of the sectional planes corresponding to the A, B and C sectional planes by the user.

Next, the interface device 318 receives the information of the screen layout from the user and then outputs a command so that the sectional plane images are displayed according to the information. The screen layout, which is a configuration figure representing how many sectional plane images are displayed on the screen of the display device 303, can be automatically determined according the number of the sectional plane images of the target object to be displayed. There are selectable layouts of 1*1 (one sectional plane image in a horizontal direction of the display device and one sectional plane image in a vertical direction of the display devices 2*1, 2*2, 3*2, 4*3, 6*4 and the like.

Lastly, the interface device 318 receives the information of the display region from the user and outputs a command so that an image corresponding to the display region is displayed only on the screen of the display device. The display region, which indicates the size of an image of the target object to be displayed on the screen of the display device, can be set directly on the display device 303 or by inputting coordinates through a mouse or the like by the user. According to the above configuration, since the scan conversion of the 3D ultrasound data of the target object corresponding to a region, which is not substantially displayed, is not required, a data processing speed can be improved. A detailed description will be mentioned later.

The determination unit 312 determines whether the 3D data of the target object is received from the probe. Or, the 3D data storage device 317 in accordance with that of the display region is changed on the basis of the information of the display region from the interface device 318. More particularly, if it is required that a current image of the target object has to be displayed in real time whenever the probe acquires the data of the target object, the 3D data is received from the probe 301. If it is required that the scan is virtually performed by using the data stored beforehand, the 3D data of the target object is received from the data storage device 317, which will be described later.

The display region is changed when the user enlarges the display region or the displayed 3D image becomes rotated, moved or expanded. Even if the display region is not changed when the target object is first scanned, it can be determined that the display region may be changed. As illustrated in FIG. 3B, when the display region is changed, the determination unit 312 outputs the information related to the 3D data of the target object and the display region to the display region calculation unit 313. When the display region is not changed, the determination unit 312 outputs the information related to the 3D data of the target object and the display region to the rendering look-up table storage unit 315. A case outputted to the rendering look-up table storage unit 315 will be described later.

Figure 1:
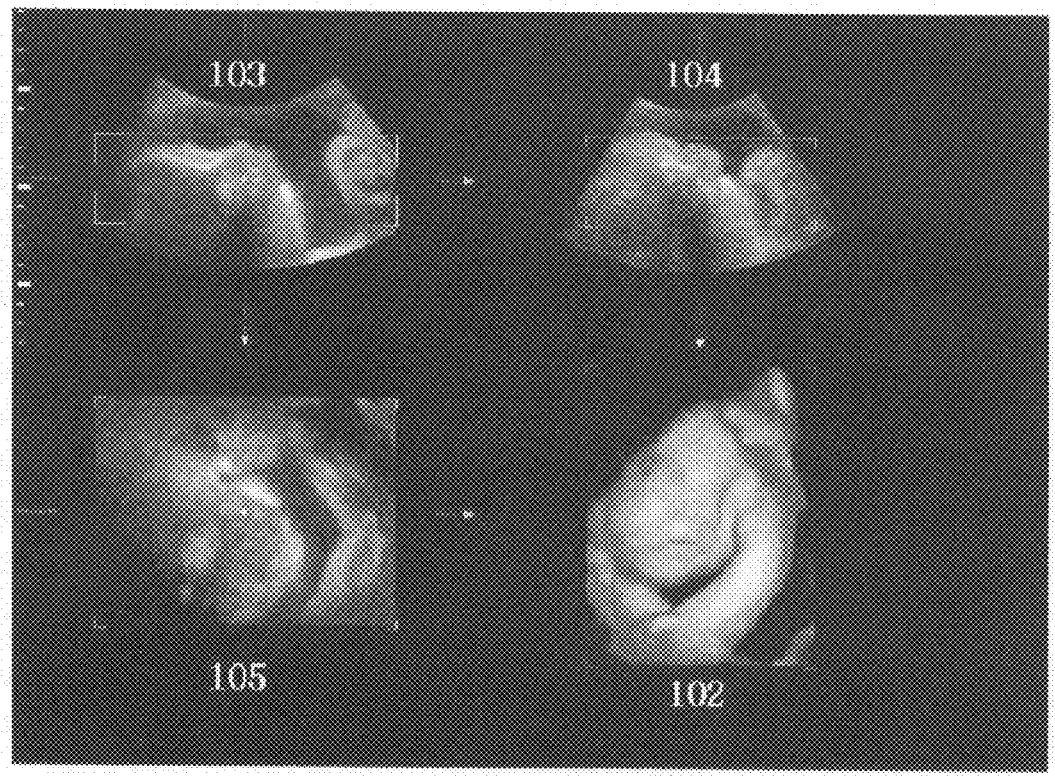
FIG. 1 is a photograph showing 3D ultrasound image of a target object according to a conventional 3D ultrasound diagnostic device.
Figure 2A:
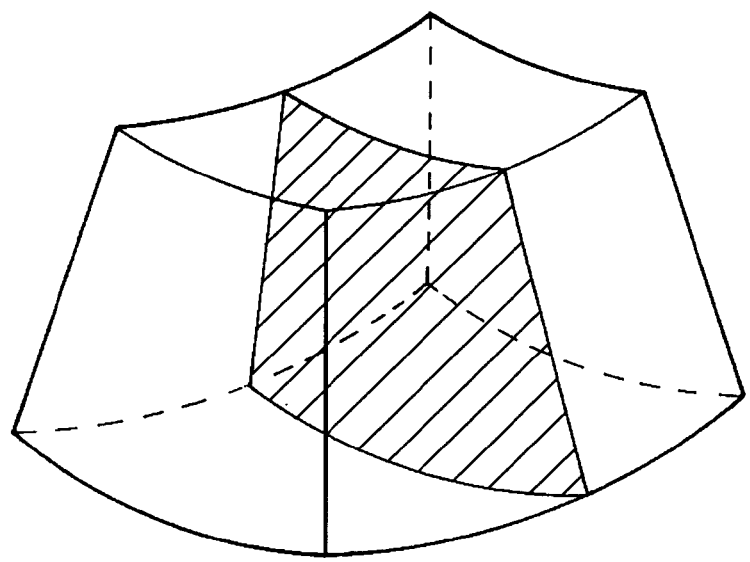
FIGS. 2A to 2C schematically show A, B and C sectional planes to be used as a reference sectional plane of images of FIG. 1.
Figure 2B:
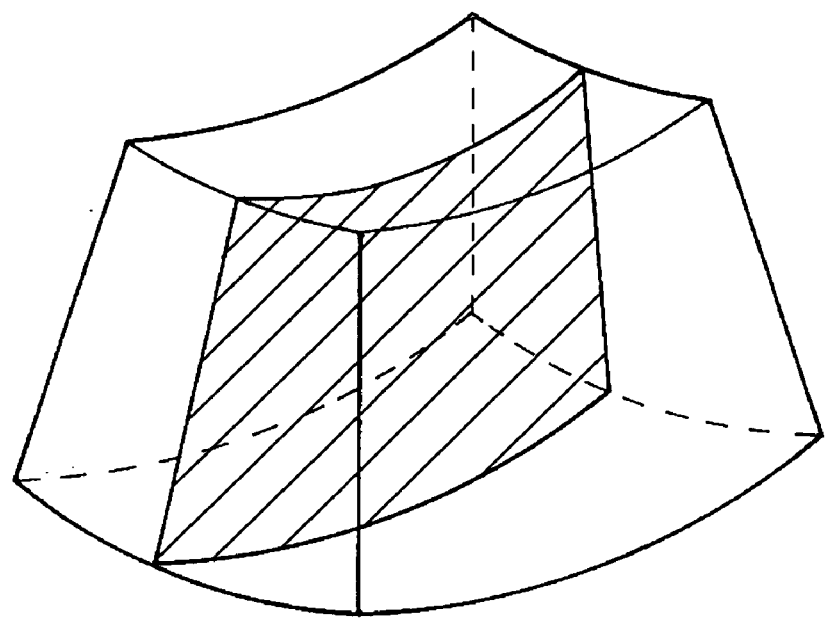
Figure 2C:
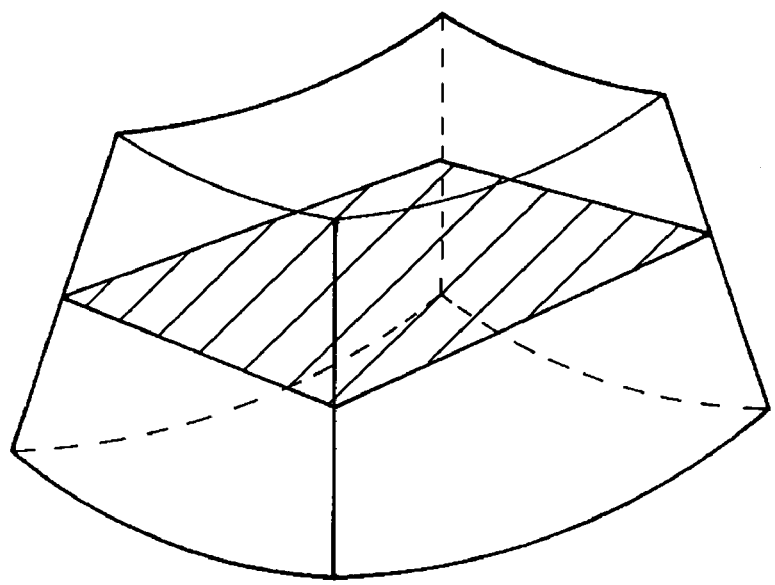

The display region calculation unit 313 calculates Cartesian coordinates of x, y and z in the displayed region in which the ultrasound images 102 to 105 as the view 101 illustrated in FIG. 1 are substantially displayed. The display region calculation unit 313 outputs the 3D data of the target object received through the determination unit 312 without any special process.

The scan conversion unit 314 receives conical coordinates of the 3D data of the target object and the Cartesian coordinates of the x, y and z calculated in the display region calculation unit 313. It then converts the Cartesian coordinates to the conical coordinates of the 3D data of the target object based on the Cartesian coordinates of x, y and z (Scan Conversion). The reason for converting the data is because the 3D ultrasound data received from the probe 301 is not based on the Cartesian coordinates but rather based on the conical coordinates. The display region displayed on the display device is based on the Cartesian coordinates. In order to perform the scan conversion, a complicated mathematical operation such as an arc tangent operation should be carried out. Whenever the 3D data of the target object is received, if the arc tangent operation is carried out, it requires a long operation time. Therefore, the target object cannot be displayed in real time.

In order to solve the above problem, a geometric look-up table, which stores indices matched with the 3D Cartesian coordinates of the screen and arc tangent operation resulting values corresponding to each index of 3D data, is produced. The geometric look-up table is stored in the geometric look-up table storage unit 311. According to the above configuration, the Cartesian coordinates of the display region can be rapidly scan converted to the conical coordinates of the 3D data of the target object for a 3D rendering process. This is so that the image of the target object can be displayed in real time.

Hereinafter, a process for generating the geometric look-up table will be described. Generally, the geometric look-up table should be produced before the 3D data of the target object is received from the probe 301 in accordance with the present invention.

Figure 4A:
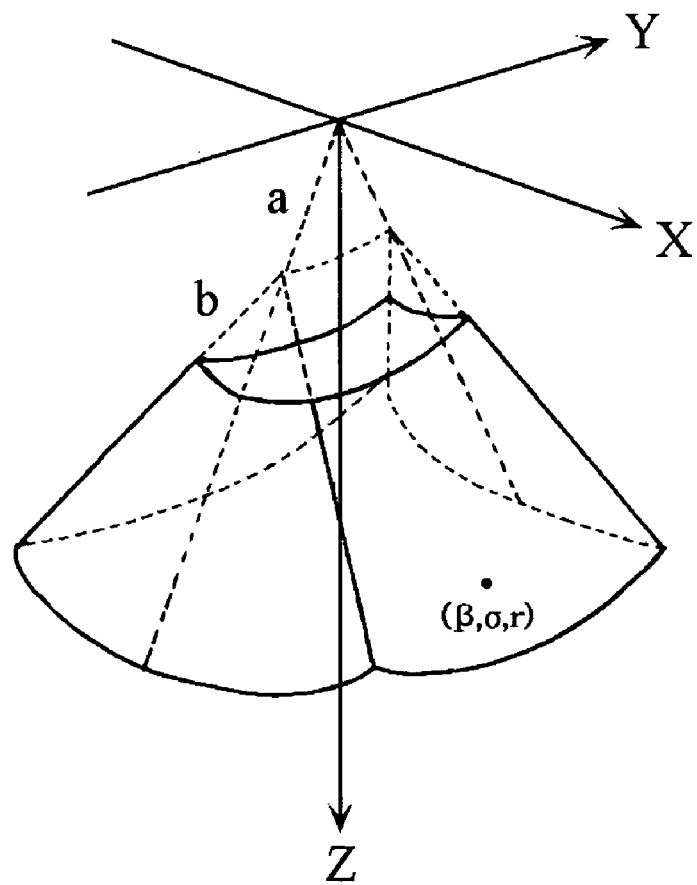
FIGS. 4A to 4C are diagrams showing relations between the Cartesian coordinates and the conical coordinates used in accordance with the present invention.
Figure 4B:
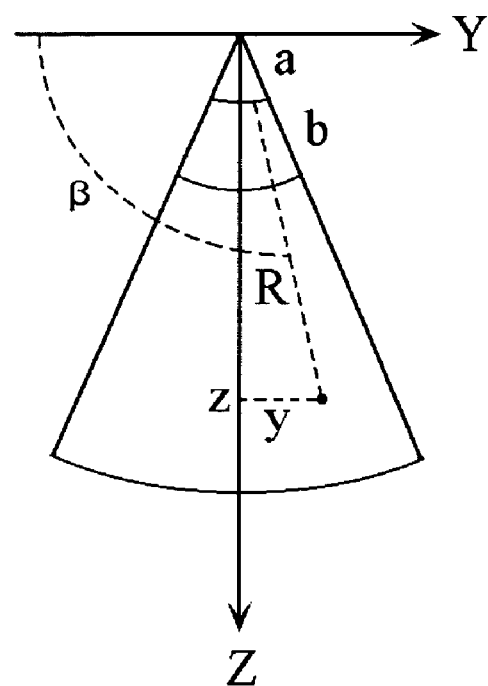
Figure 4C:
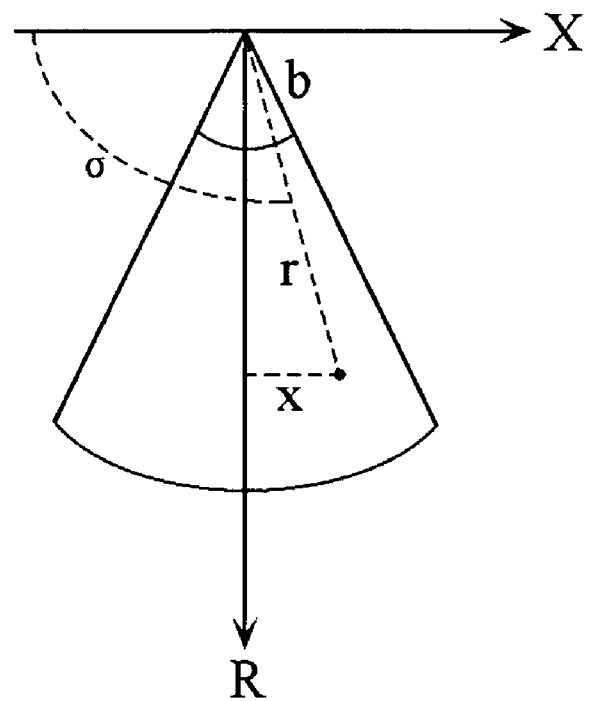

FIG. 4A is a diagram showing the relation between the conical coordinates and the Cartesian coordinates. FIG. 4B is a diagram illustrating an arbitrary 3D data shown in FIG. 4A in a Y-Z Cartesian coordinates. FIG. 4C is a diagram illustrating an arbitrary 3D data shown in FIG. 4A in a X-R Cartesian coordinates. The axes of X, Y and Z are to configure a 3D Cartesian coordinates in which the image of the target object can be displayed. R axis is an axis perpendicular to the X axis from a portion in which the 3D ultrasound image is acquired.

Accurate conical coordinates of ($\beta,\sigma,r$), in which 3D data to be scan-converted from the Cartesian coordinates of the 3D data are located, can be obtained as a following equation.

$$R = \sqrt{y^2 + z^2} - a^2 \quad (1)$$

$$\beta = \frac{\pi}{2} + \tan^{-1}\left(\frac{y}{z}\right), \ \sigma = \frac{\pi}{2} + \tan^{-1}\left(\frac{x}{R}\right), \ r = \sqrt{x^2 + R^2} - b^2$$

Wherein, $\beta$ represents a scan viewing angle, which corresponds to a swing angle range of a stepping motor in the probe, ranging from 0° to 180°; $\sigma$ represents a probe viewing angle, which corresponds to a width angle range of a 2D image scanned from the probe 301, ranging from 0° to 180°; r represents a distance from a portion in which the ultrasound image is acquired to an arbitrary 3D data; a represents a distance from an angular point of the scan viewing angle to an angular point of the probe viewing angle; and b represents a distance from an angular point of the probe viewing point to the portion in which the ultrasound image is acquired. Also, x, y and z represent the overall values of X, Y and Z axes.

In order to obtain the conical coordinates of $\beta$ and $\sigma$ from Equation 1, the arc tangent operations of $\tan^{-1}(y/z)$ and $\tan^{-1}(x/R)$ have to be first performed. The x, y and z in the arc tangent equation are set values corresponding to the Cartesian coordinates of the screen of the display device. R is calculated from the x, y and z as shown in Equation 1. The following tables 1A and 1B show calculations of R and r. After obtaining R by performing a parallel processing for arbitrary 4 numbers of y existing in the Y axis and arbitrary 4 numbers of z existing in the Z axis, r is calculated by performing a parallel processing for arbitrary 4 numbers of z existing in the X axis and r. When the x, y and z are processed by the parallel processing (as described the above), the speed for the scan conversion of the 3D data can be improved.

TABLE 1A

| m1 = [y4, y3, y2, y1] | Input y to m1 |
| m5 = m1 × [y4, y3, y2, y1] | m5 is a square of y |
| m2 = [z4, z3, z2, z1] | Input z to m2 |
| m6 = m2 × [z4, z3, z2, z1] | m6 is a square of z |
| m7 = m5 + m6 | m7 is equal to y2 + z2 |
| m3 = sqrt(m7) | m3 is a square root of y2 + z2 |
| m8 = m3 − a | m8 is [R4, R3, R2, R1] |

TABLE 1B

| m0 = [x4, x3, x2, x1] | Input x to m0 |
| m4 = m0 × [x4, x3, x2, x1] | m4 is a square of x |
| m5 = [R4, R3, R2, R1] | Input R to m5 |
| m5 = m5 × [R4, R3, R2, R1] | m5 is a square of R |
| m9 = m4 + m5 | m9 is equal to x2 + R2 |
| m10 = sqrt(m9) | m10 is a square root of x2 + R2 |
| m11 = m10 − b | m11 is [r4, r3, r2, r1] |

As shown above, the arc tangent operations of $\tan^{-1}(y/z)$ and $\tan^{-1}(x/R)$ are calculated according to the values of x, y and z and values of R corresponding thereto. As indexes corresponding to (y/z) and (x/R) are given to the resulting values of the calculated arc tangent operation, the geometric look-up table is generated. The geometric look-up table includes:

indices representing $\left(\frac{y_1}{z_1}\right), \left(\frac{y_2}{z_2}\right), \ldots, \left(\frac{y_n}{z_n}\right)$;

angles of $\tan-1\left(\frac{y_1}{z_1}\right), \tan-1\left(\frac{y_2}{z_2}\right), \ldots, \tan-1\left(\frac{y_n}{z_n}\right)$;

indices representing $\left(\frac{x_1}{R_1}\right), \left(\frac{x_2}{R_2}\right), \ldots, \left(\frac{x_n}{R_n}\right)$; and angles of $\tan-1\left(\frac{x_1}{R_1}\right), \tan-1\left(\frac{x_2}{R_2}\right), \ldots, \tan-1\left(\frac{x_n}{R_n}\right)$.

The scan conversion unit 314 retrieves the index matched with the 3D conical coordinates and the resulting values of the arc tangent operations corresponding to the index by using the geometric look-up table stored in the geometric look-up table storage unit 311, which is previously produced. As the retrieved resulting value of the arc tangent operation is applied to the Equation 1, the conical coordinates of (β1, σ1, r1), (β2, σ2, r2), . . . , (βn, σn, rn) corresponding to the coordinates of (x1, y1, z1), (x2, y2, z2), . . . , (xn, yn, zn) can be acquired.

Next, the scan conversion unit 314 converts the Cartesian coordinates of display region to the conical coordinates of the 3D data. It then outputs the converted 3D data, the conical coordinates in which the 3D data are located and the index retrieved from the geometric look-up table storage unit 311.

As mentioned above, the scan conversion unit 314 performs the scan conversion after finding the conical coordinates in which the 3D data of the target object are located. This can be done by performing the parallel processing of the x, y, z and R, which are previously set, by using the resulting values of the arc tangent operation included in the geometric look-up table storage unit 311 (instead of directly performing the arc tangent operation requiring a long operation time). Thus, the speed for scan-converting the Cartesian coordinates of the display region to the conical coordinates of the 3D data of target object can be improved.

The rendering look-up table storage unit 315 receives the data from the scan conversion unit 314 if the determination unit 312 determines that the display region is changed (and from the determination unit 312). In case of receiving the data from the scan conversion unit 314, the index and the conical coordinates corresponding to the 3D data are received. Then, a rendering look-up table including the received index and the conical coordinates is produced and stored. Thereafter, the scan-converted 3D data are outputted. The reason for producing and storing the rendering look-up table is as follows. When the display is not changed, since the Cartesian coordinates of display region are scan-converted to the conical coordinates, if the resulting values of the scan conversion are previously stored (instead of performing the identical scan conversion again), a data processing speed of the ultrasound diagnostic system can be improved.

Meanwhile, in case of receiving the conical coordinates of the 3D data of the target object from the determination unit 312 because the display region is not changed, the Cartesain coordinates corresponding to the previous display region are retrieved. Then, the conical coordinates of the 3D data corresponding to the Cartesian coordinates are outputted.

In detail, when the display region is not changed, the conical coordinates of the 3D data of a new target object, which are scan-converted from the Cartesian coordinates of the display region, are identically located with the Cartesian coordinates of the display region of the prior target object. For example, since the 3D data of a first target object located in the conical coordinates of (βn, σn, rn) and the 3D data of a second target object located in the conical coordinates of (βn, σn, rn) are scan-converted from identical Cartesian coordinate values of (xn, yn, zn) of display region (even if the target object is changed), the indices matched with the conical coordinates of the 3D data are identical to each other. As such, it is not required to pass the display region calculation unit 313 and the scan conversion unit 314.

On the other hand, an operation frequently changing the display region such as continuous movement or enlargement of the displayed image can be performed. Since performing the scan conversion together with generating and storing the rendering look-up table at each time can give more loads to the system, the data can be transmitted from the scan conversion unit 314 and the rendering unit 316 without producing the rendering look-up table in the rendering look-up table storage unit 315.

The rendering unit 316 renders as many as the number of layouts selected by the interface device 318 by using the 3D data of the target object received from the rendering look-up table storage unit 315 and the scan conversion unit 314. The rendering unit 316 displays an image of multiple sectional planes of the target object by projecting the received 3D data to the 3D coordinates of the display region. If the image is exceeded over one screen because the number of the sectional planes of the layout is too many, the image of the next sectional plane can be shown by using a scroll function of the windows or the like. The multiple sectional planes are the plurality of sectional planes of the target object parallel with a reference sectional plane in the vertical direction of the reference sectional plane A process for rendering the 3D data is carried out identical to the direct volume rendering process, which is typically used. As such, a detailed explanation will be omitted herein.

In the display, the multiple sectional planes can be displayed according to a distance from the reference sectional plane If necessary, the multiple sectional planes can be displayed according to an absolute depth from a surface of the target object. Also, the user can adjust the distance between the sectional planes through the interface device. This is so that the diagnosis can be carried out by showing the sectional plane images for a more minute depth.

Figure 5:
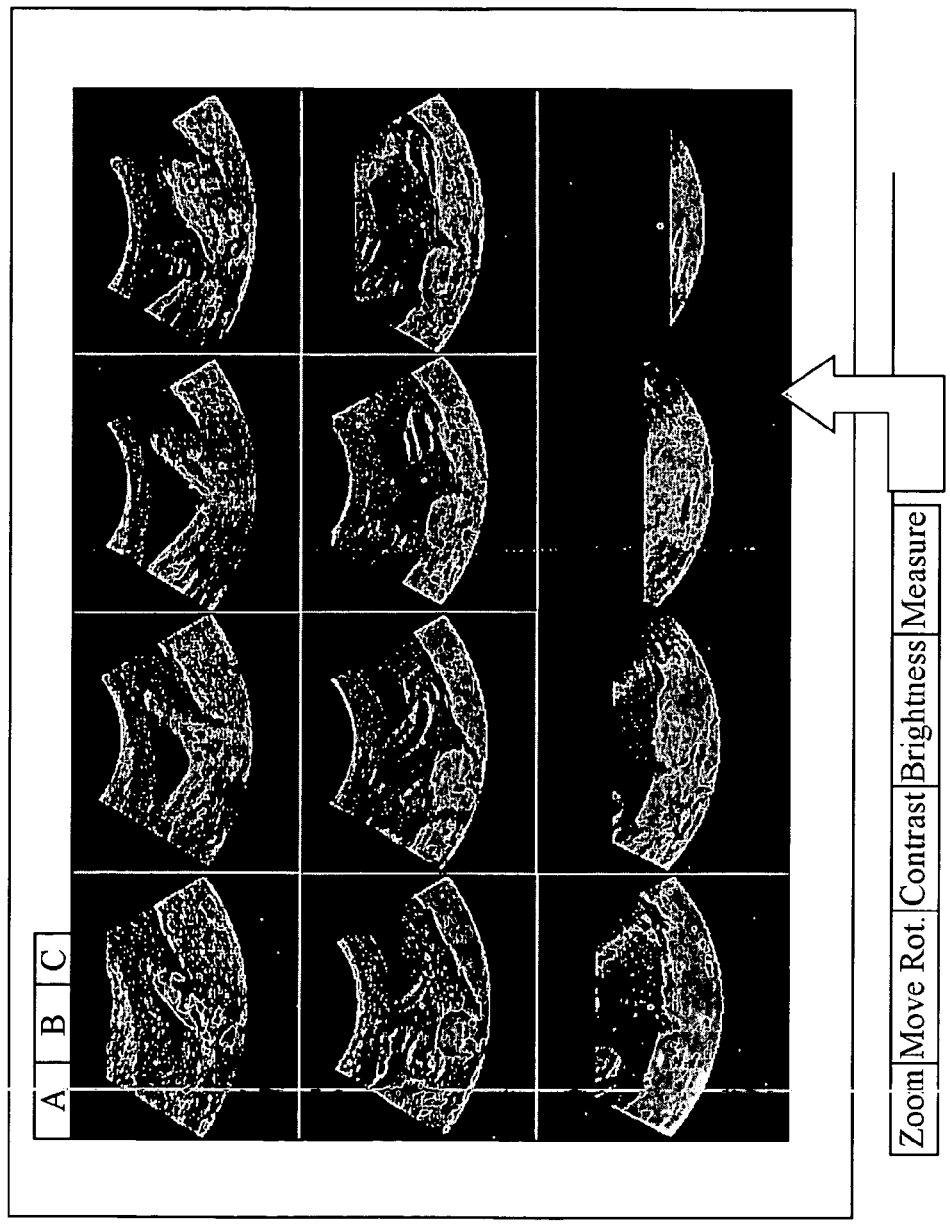
FIG. 5 is a photograph showing images of the multiple sectional planes displayed in accordance with the present invention.

FIG. 5 is a photograph showing ultrasound images of the multiple sectional planes displayed after performing the rendering. In FIGS. 5A, B and C represent the reference sectional planes of the A, B and C sectional planes, respectively. The displayed images are changed by which one of the reference sectional planes is selected by the user. Also, various view operation commands, which process the displayed image, are denoted at the bottom portion. The user can zoom in/out, delete or move the displayed image (as the image is edited in a picture plate of the Windows) by using the view operation commands.

The user can find the desired image by moving the probe showing the displayed multiple sectional plane images. As the above data process is repeatedly carried out, the sectional plane image of the target object is displayed in real time. When the desired image is found, the real-time status is stopped and the 3D data can be stored in the data storage device 317. Therefore, even if the target object does not exist afterwards, the target object can be virtually scanned by using the stored data.

In case of virtually performing the scan process, the determination unit 312 receives the 3D data of the target object from the 3D data storage device 317. If it is requested to display the current sectional plane images of the target image by acquiring the 3D data of the target object in real time, the determination unit 312 receives the 3D data the target object from the probe 301. If it is requested to virtually scan the target object by using the previously stored data, the 3D data of the target object are received from the 3D data storage device 317.

The 3D data storage device 317 may include various volatile storage devices and/or non-volatile storage devices. The non-volatile storage device may include a read only memory (ROM), a programmable read only memory (PROM), an electrically programmable read only memory (EPROM) and an electrically erasable programmable read only memory. The volatile storage device may include a random access memory (RAM), a synchronous RAM (SRAM), a dynamic RAM (DRAM), a synchronous DRAM (SDRAM), a double data rate SDRAM (DDR SDRAM) and a direct RAM bus (DRRAM). Also, it may include a memory device such a magnetic disk drive, a floppy disk drive, a tape drive, a Zip drive, a flash memory card, a memory stick, compact disk ROM (CD-ROM), a CD recordable drive (CD-R), a CD rewriteable drive (CD-RW drive), a digital versatile ROM drive (DVD ROM) or the like. However, the storage device is not limited only to the above storage devices.

The user can display the multiple sectional plane images by using the stored 3D data, that is, through the virtual scan. Since the procedure processing the 3D data of the target object received from the 3D data storage device 317 is identical to the procedure processing the 3D data of the target object received from the probe 301, a detailed explanation will be omitted herein.

When the 3D data of the target object is received through the 3D data storage device 317, it is not required that the number of the layouts to be displayed is equal to the number of the layouts used in acquiring the 3D data. Further, the number of the layouts means the number of sectional planes that the user wants to see. As such, if the user intends to see an image of different sectional plane or different depth from the stored data, the required data can be generated and rendered by using an interpolation or the like.

An oblique sectional plane view, which will be described later, can be applied to the displayed image. The data can be used to the next operation by storing the final result.

Also, as the user moves, zooms in/out and rotates the displayed images, or changes the display region, clinical information for the target object by observing the varied ultrasound images can be obtained.

The movement, enlargement or reduction in the image of the multiple sectional planes can be implemented through an image processing technique without performing the process (as described in FIG. 3B) for improving the processing speed.

There are roughly four merits obtained when the target object is displayed according to the above process.

First, when the target object is dynamic such as a heart, blood flow or the like, the user can identify a set of sectional plane images representing different locations for each scan direction at once in real time by using the multiple sectional plane images. This is so that the diagnosis can be rapidly and accurately implemented.

Second, the user can better accurately determine whether a displayed portion corresponds to the desired data. An ultrasound diagnostic system scans the target object by moving the probe with a hand's movement. It is possible that an inaccurate location is scanned due to the hand's movement. However, in accordance with the present invention, the user can identify the desired image through the real-time multiple sectional plane images and accurately perform the diagnosis through various image processes again in the multiple sectional plane images of a static state by storing the desired volume data.

Third, since the scanned data are stored in the 3D data storage device, even if the target object does not exist, the multiple sectional plane views can be displayed the same as the target object exists and the oblique sectional plane view can be displayed.

Lastly, the operator can perform various image processes for the displayed image and the oblique sectional plane view function. This is so that the desired image can be more freely displayed.

II. Oblique Sectional Plane Image

Since the conventional 3D ultrasound diagnostic system displays A sectional plane, B sectional plane and C sectional plane, which perpendicularly section an image of the 3D data at a specific location as illustrated in FIG. 1 and shows an arbitrary sectional plane through rotation of the displayed sectional plane, the sectional plane desired to be seen by the user cannot be freely displayed. Also, if the sectional planes are rotated per each location according to the prior art, it is difficult to know the location of the current sectional plane and find the desired sectional plane. Therefore, the present invention provides the oblique sectional plane view function capable of making the desired sectional plane to be directly seen at an image of a reference sectional plane by the user.

In accordance with the present invention, the user draws an arbitrary straight line or curved line on the reference sectional plane. Then, a plane or a curved surface extended in a vertical direction of the reference sectional plane from the drawn straight line or curved line will be finally displayed in accordance with the oblique sectional plane image display method of the present invention.

Figure 6:
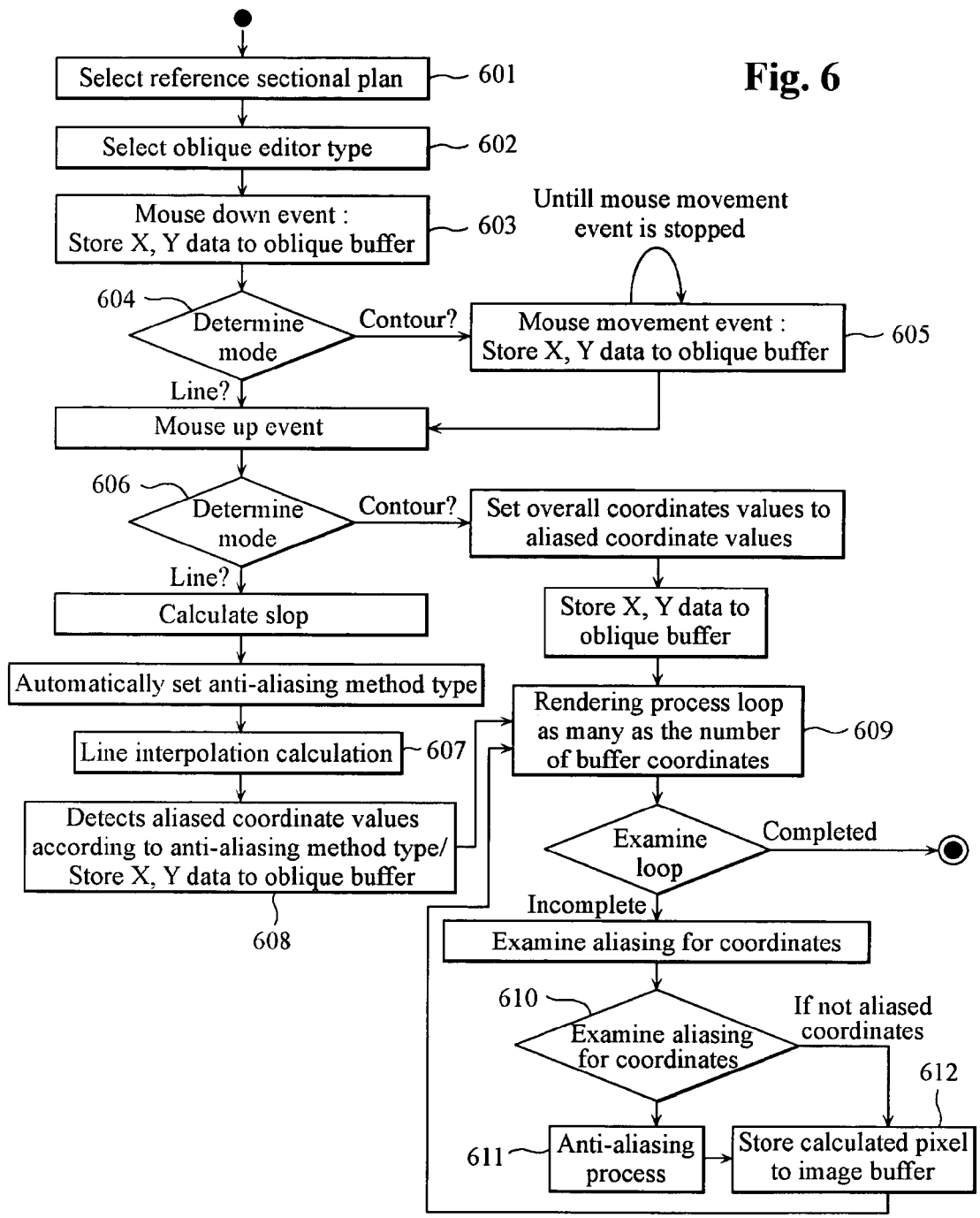
FIG. 6 is a flow chart explaining a display of an oblique sectional plane in accordance with the present invention.

The preferred embodiment of the present invention will be described below in detail in view of FIG. 6.

First, after the user displays the real-time multiple sectional plane images of, for example, A sectional plane, B sectional plane or C sectional plane of the target object, with the same method used for showing the multiple sectional plane images of the target object as mentioned above, one of the sectional planes is selected as the reference sectional plane at the step 601. Of course, the selectable sectional plane image can be displayed by using a conventional 3D data acquisition method (not the above real-time method) and the 3D data, which have been already stored in the storage medium.

Next, the user determines whether the arbitrary line is represented with the straight line (line mode) or the curved line (contour mode) at the step 602. The reason why one line of the straight and curved lines is selected is because an anti-alias method can be different according to each line.

For example, if the user pushes a mouse button in a computer for drawing the arbitrary line on the reference sectional plane according to the selected mode, the coordinates of a mouse pointer at that time is stored in a buffer at step 603. In accordance with the present invention, the mouse is used as an example to draw the arbitrary line. Also, another input device, such as a touch pad or the like, can be used instead of the mouse.

When the user pushes the mouse button, if a line type selected by the user is the straight line, a line processing is performed. If the line type is the curved line, it is moved to a step processing the mouse movement at step 604. In order to display the straight line, start coordinates and end coordinates of the mouse pointer are only required. On the other hand, in order to display the curved line, the overall coordinates are required in moving the mouse. Thus, the processes are different from each other.

The line mode indicating the straight line is on standby until a mouse up event generated when a click button of the mouse is released is generated. In the contour mode indicating the curved line, the overall coordinates in moving the mouse are continuously stored in a buffer (hereinafter, referred to as an oblique buffer) at the step 605.

Next, when the user stops moving the mouse and releases the mouse button, an arbitrary segment line, which the user indicates, have to be displayed.

Figure 7A:
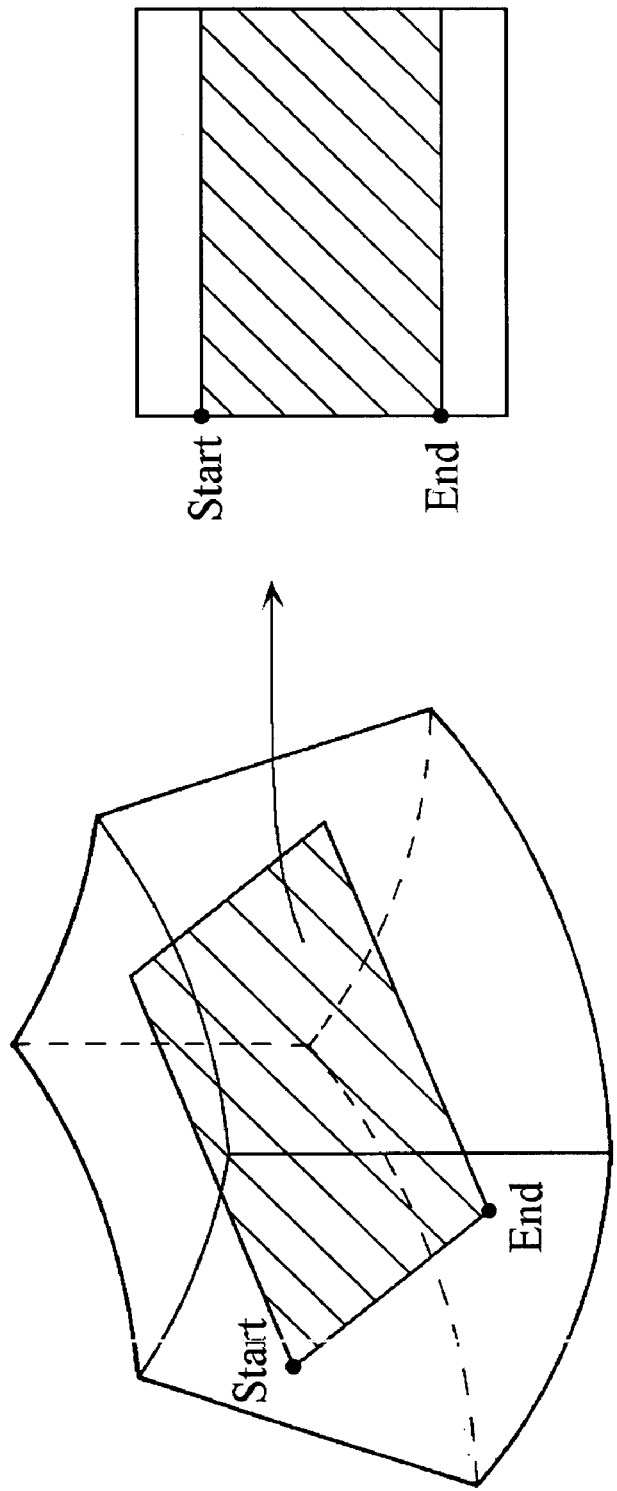
FIGS. 7A to 7D are schematic diagrams showing sectional planes representing lines on each reference sectional plane in accordance with the present invention.
Figure 7B:
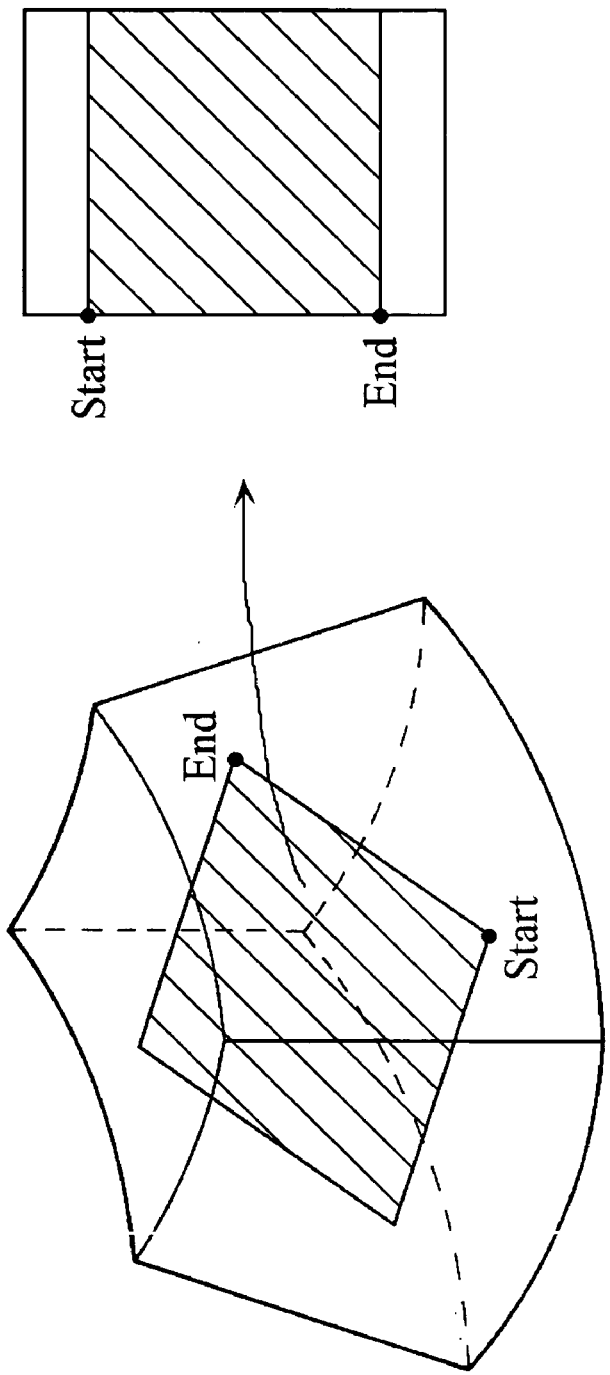
Figure 7C:
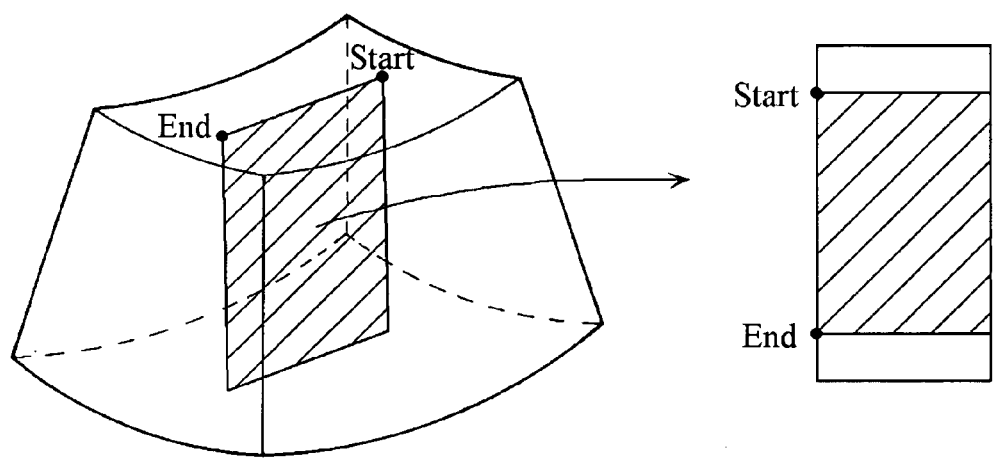
Figure 7D:
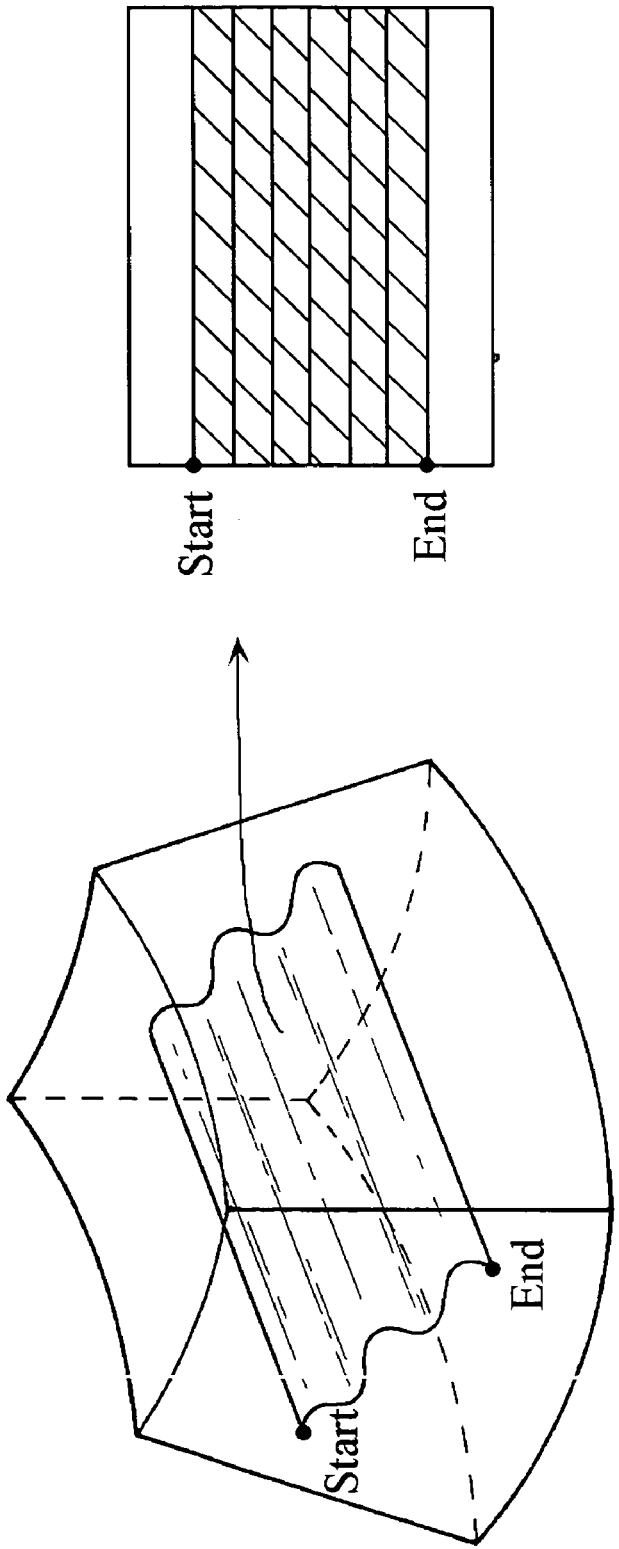

For example, according to the steps from 601 to 605, after the user selects the A sectional plane as the reference sectional plane, a desired sectional plane in the displayed A sectional plane is indicated (as shown in FIG. 7A). A starting point is a point that the user starts to draw the line and an ending point is a point that the user ends to draw the line (as shown in FIG. 7A). If the lines are indicated on the A sectional plane as above, a dashed region (as illustrated at a right side in FIG. 7A) is displayed after an anti-aliasing process is performed. FIGS. 7B and 7C show the B and C sectional planes. FIG. 7D shows the sectional plane obtained by drawing the curved lines (as illustrated in FIG. 7A) on the A sectional plane.

Figure 8A:
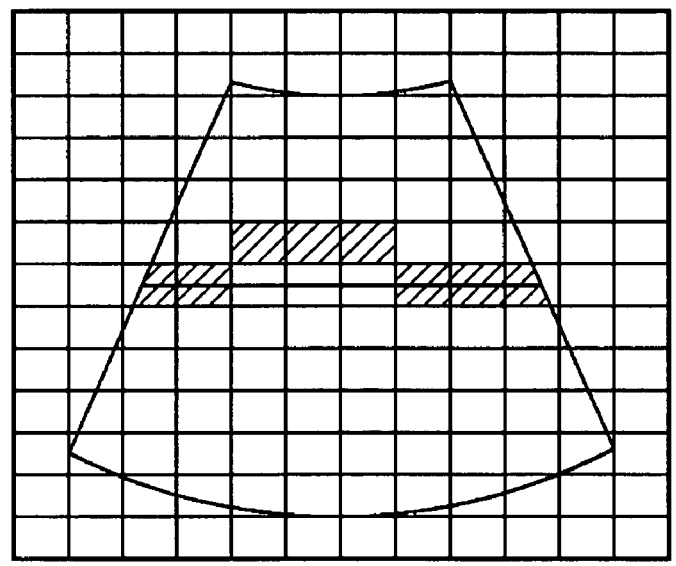
FIGS. 8A to 8C are schematic diagrams showing cases generating aliasing in the sectional planes of FIGS. 7A to 7D.
Figure 8B:
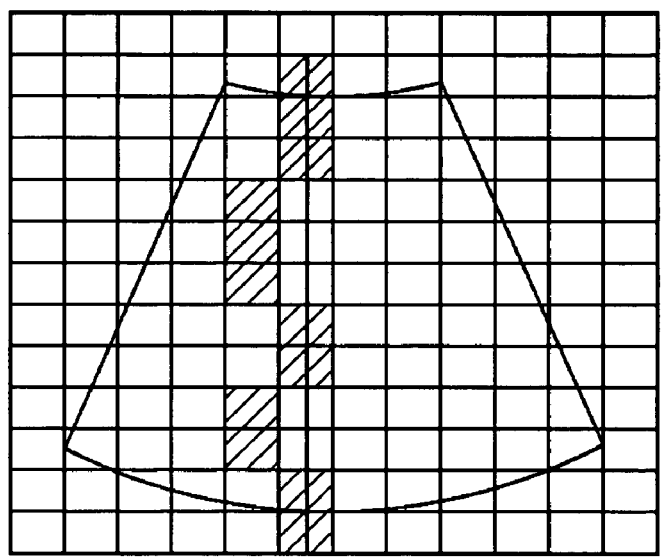
Figure 8C:
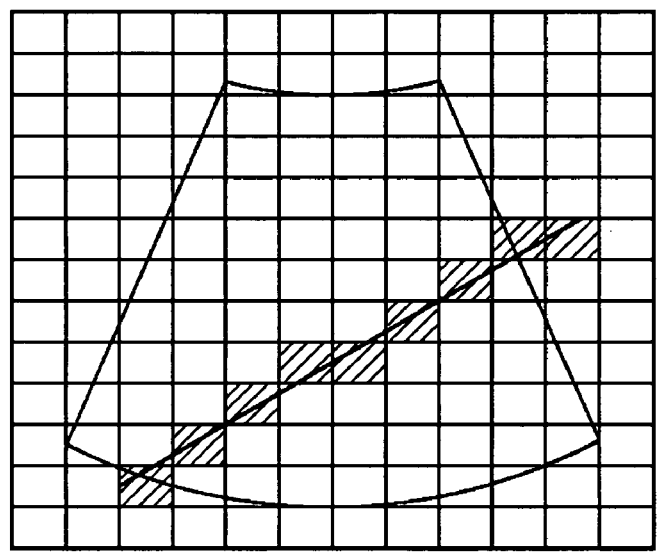

Since the straight lines or the curved lines drawn by the user are drawn on the monitor screen, the lines are not consecutively drawn. Also, since the image information of the monitor screen is represented through 2-dimensionally arrayed dots, if the dots are of the small number, the lines may not be smooth due to a jagged staircase effect. As shown in FIG. 8A, even though the user tries to represent the straight line in a horizontal direction of the reference sectional plan, the user may not see the straight line but the dashed region due to the aliasing phenomenon. FIGS. 8B and 8C show that the aliasing is generated when the user tries to draw the straight line in a vertical direction or an inclined direction of the reference sectional plane An anti-method, aliasing method, which is introduced for solving the above problem, is an image processing technique smoothly representing the image by adding dots of an intermediate color of the background and the line between each dot. A selective anti-aliasing technique can be employed instead of the general anti-aliasing technique in accordance with the present invention.

The selective anti-aliasing technique is not to apply the anti-aliasing technique to the overall segment data of the lines but to apply the anti-aliasing technique only to the segment data in which the aliasing is generated by a regulated rule.

The selective anti-aliasing technique is classified according to slopes of the segments of the lines.

If the slope of the segment is $d=\Delta y/\Delta x$, wherein $\Delta x=X\max-X\min$ (Xmax is the maximum X coordinates of the segment and the Xmin is the minimum X coordinates) and $\Delta y=Y\max-Y\min$ (Ymax is the maximum X coordinates of the segment and the Ymin is the minimum Y coordinates), then there are three cases at the slope of the segment, as shown below:

1) $d\approx 0$: $\Delta x$ is much greater than $\Delta y$;
2) $d\approx\infty$: $\Delta y$ is much greater than $\Delta x$; and
3) $0<d<\infty$: the slope exits.

In case of 1), it may be that a component of an x-axis only exits and a y value of pixel coordinates is not fixed. Therefore, when the y value is compared by the previous value at each coordinates, if the comparison result is different from each other, the coordinates of y may correspond to the coordinates that the aliasing is generated as shown in FIG. 8A.

In case of 2), it may be that a component of a y-axis only exits and an x value of pixel coordinates is not fixed. Therefore, when the x value is compared by the previous value at each coordinates, if the comparison result is different from each other, the x coordinates of x may correspond to the coordinates that the aliasing is generated as shown in FIG. 8B.

In case of 3), since the slop exits, when each pixel coordinates of the segment is differently located, the aliasing may be generated.

When the mouse movement is stopped and the mouse click button is released (in the line mode as described above), the slope of the straight line is calculated and then the anti-aliasing method is automatically set and used. In the contour mode, the coordinate values in the oblique buffer are used as the aliased data. Next, a line interpolation calculation is performed to produce the coordinate data between the first coordinates and the last coordinates in the case of the line mode at the step 607. Thereafter, the coordinate data are determined whether the data corresponds to the aliased data by the slope whose coordinates is previously calculated as a reference to thereby detect the aliased data. The interpolated coordinates are stored in the oblique buffer.

Next, a rendering process is carried out by rotating a loop as many as the number of the coordinates of the oblique buffer, which are previously stored at the step 609. The coordinates are determined whether the coordinates are the aliased coordinates or not by carrying out the rendering process for each coordinates in a direction of the depth.

Figure 9:
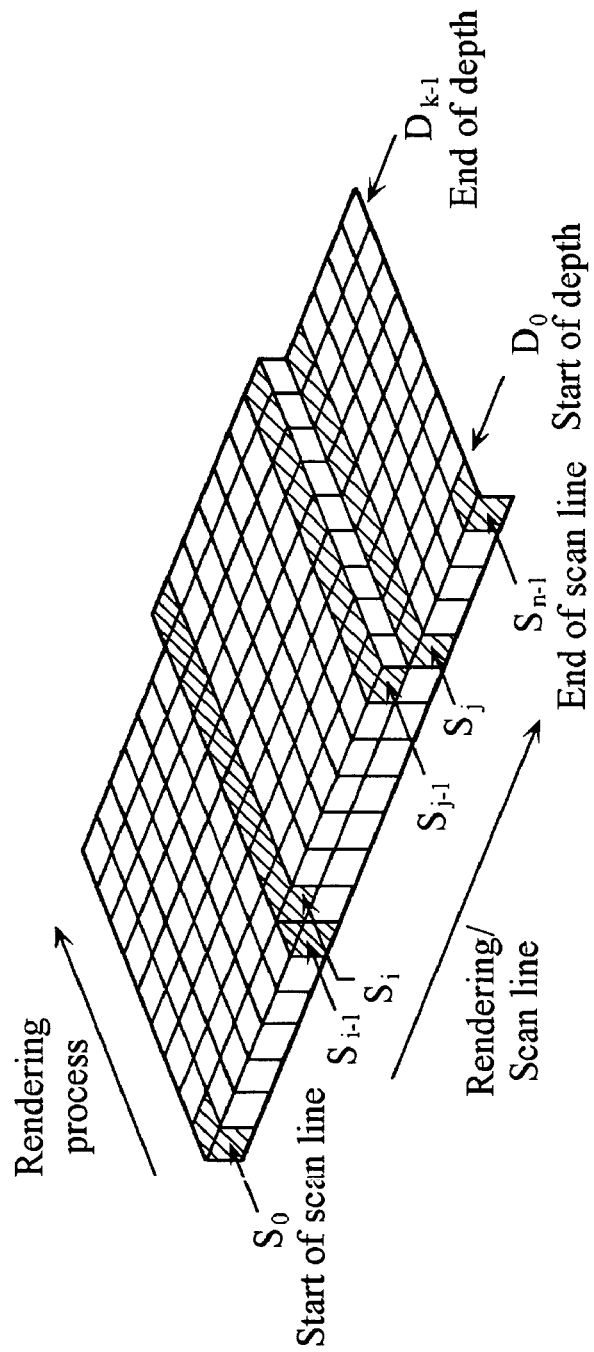
FIG. 9 is a diagram showing a rendering order to display an image of a desired oblique sectional plane when the line is represented on the reference sectional plane in accordance with the present invention.

An anti-aliasing method for the aliased coordinates is carried out as shown in FIG. 9. A rendering process is carried out at each scan line. When the rendering process is carried out along the aliased scan line, the aliasing phenomenon is removed through the previous scan line value and an averaging calculation operation. The above operation is expressed as follows:

Loop $I=D0\sim Dk-1$ $Si=(Spi+Sci)/2$ $D0\sim Dk-1$: Depth index

Spi: previous data of $i^{th}$ depth
Sci: current data of $i^{th}$ depth
Si: anti-aliased data of $i^{th}$ depth That is, if the coordinates are the aliased coordinates, the anti-aliasing processing is carried out for overall data of a depth direction at the step 611. The data passing the steps 609 to 611 are stored in an image buffer at the step 612. The steps 609 to 612 are repeatedly carried out as many as the number of the oblique buffers at the step 613. The oblique sectional plane of the target object will be displayed by means of the above steps, as shown in FIG. 10.

Figure 10A:
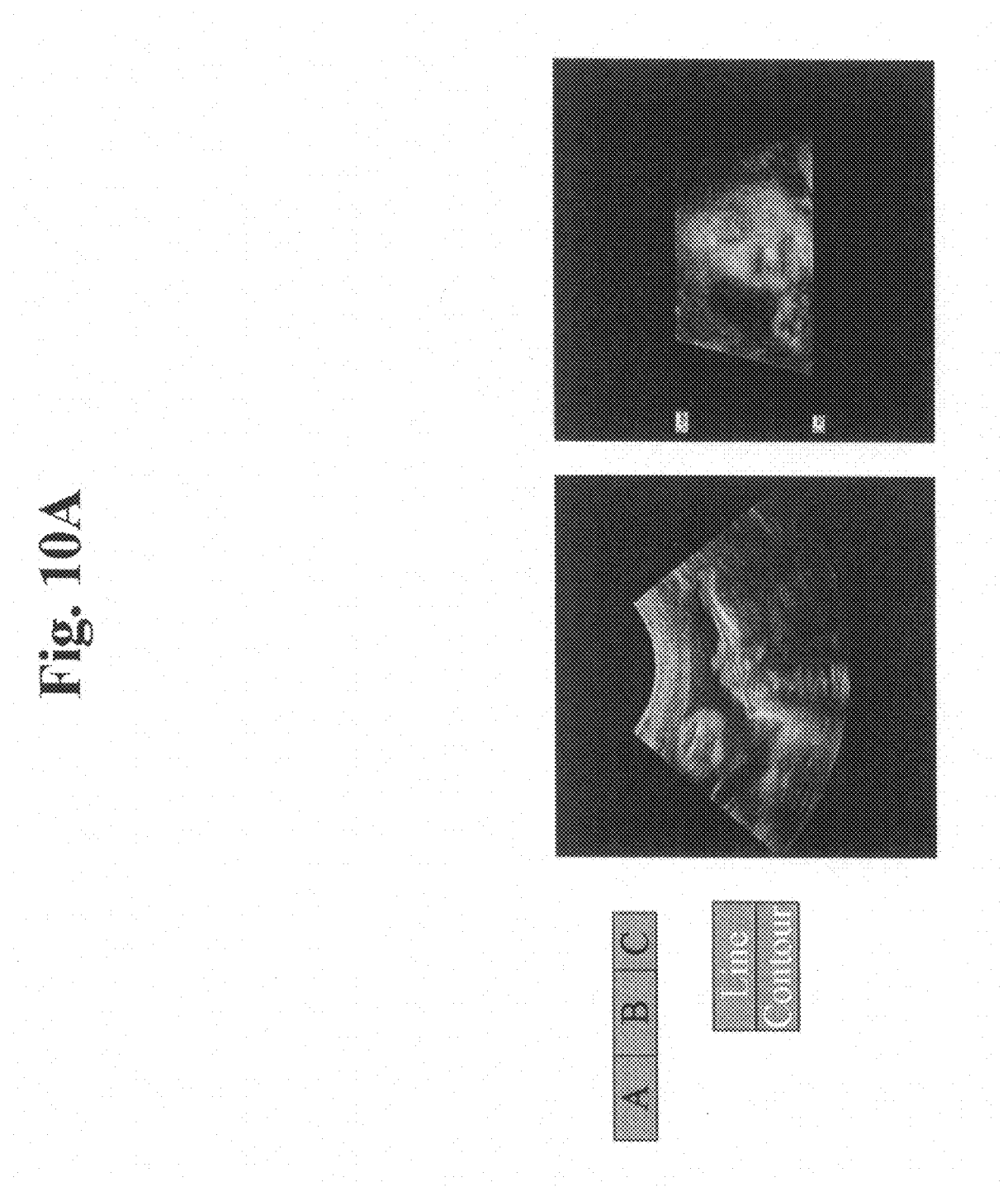
FIGS. 10A to 10C are photographs showing images for oblique sectional planes in accordance with the present invention.
Figure 10B:
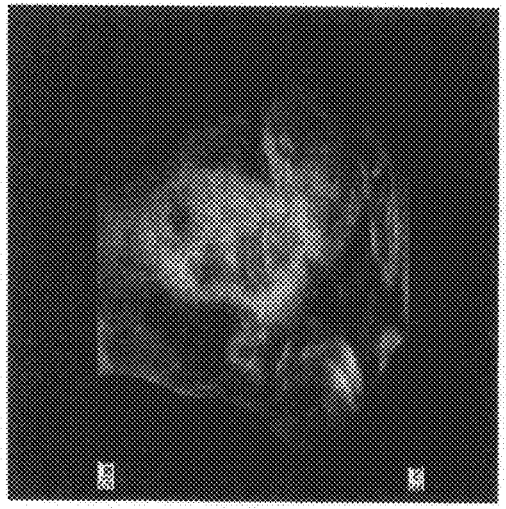
Figure 10B:
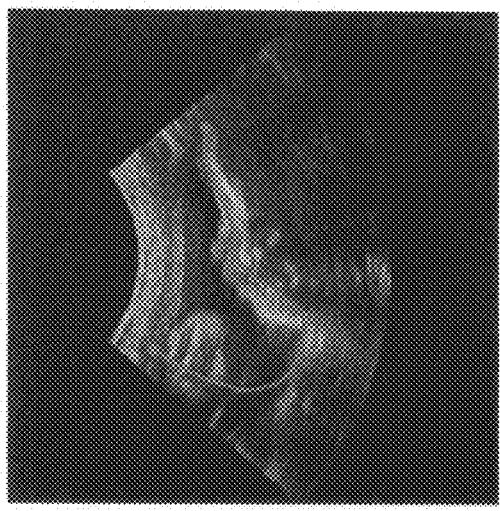
Figure 10B:
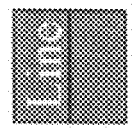

FIGS. 10A and 10B shows the displays of sectional plane images in a vertical direction of the straight line and the curved line drawn on the A sectional plane image.

Figure 10C:
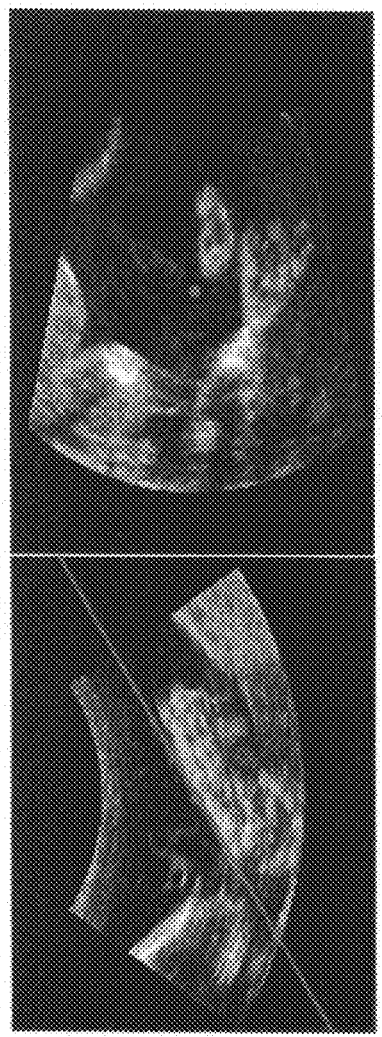
Figure 10C:

If the oblique sectional plane image is utilized, the arbitrary straight line is automatically drawn on the reference sectional plane image beforehand. This is so that it is possible that the A sectional plane image perpendicular to the straight line is displayed. As shown in FIG. 10C, since the straight line is indicated on the reference sectional plane image (e.g., the A sectional plane image), if the user pushes a certain key, the lines on the image are rotated and the sectional plane image can be displayed in a vertical direction of the straight line.

In accordance with the present invention, the target object can be scanned in real time by largely increasing the speed for performing the scan conversion of the 3D ultrasound data of the target object. Since the 3D information acquired by using the ultrasound is stored, even if the target object does not exist, the virtual scan is possible by using the stored data. Therefore, it is substantially helpful to a clinic and to a doctor treating his/her patient.

Also, the various multiple sectional plane images can be displayed differently from the prior art displaying the only reference sectional plane image of the target object and the user can select and display the desired slice image. Accordingly, it is very helpful in diagnosing the target object by using the ultrasound such as the ultrasound diagnostic device.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. An apparatus for displaying a target object by using 3-dimensional (3D) ultrasound data, comprising:
   a geometric look-up table storage unit configured to store indices of 3D data matched with Cartesian coordinates of a screen of a display device and resulting values of operations to convert the Cartesian coordinates to conical coordinates;
   a determination unit configured to receive information of a reference sectional plane from an interface device, receive the conical coordinates of the 3D data from a probe or a 3D data storage device, and determine whether a current display region displaying an image based on the 3D data of the target object is changed from a display region displaying a previous image on the screen;
   a display region calculation unit configured to calculate the display region to display the image on the screen when the display region is changed;
   a scan conversion unit configured to retrieve the indices and the operation resulting values stored in the geometric look-up table storage unit to perform scan conversion to convert Cartesian coordinates for display on the screen of the display device to conical coordinates of 3D data; and
   a rendering unit configured to render multiple sectional plane images, based on the scan-converted 3D data, parallel with the reference sectional plane.

2. The apparatus as recited in claim 1, wherein a line is arbitrarily drawn on the reference sectional plane in order to display a desired sectional plane perpendicular to the reference sectional plane taken along the line, and wherein the rendering unit renders an image of the desired sectional plane through an anti-aliasing method.

3. The apparatus as recited in claim 2, wherein the anti-aliasing method is carried out by retrieving an aliased portion in the desired section plan.

4. The apparatus as recited in claim 1, wherein the multiple sectional plane images are displayed in real time in an ultrasound diagnostic device.

5. The apparatus as recited in claim 1, wherein a desired display layout for displaying the multiple sectional plane images is selected through the interface device, and wherein the rendering unit renders the multiple sectional plane images based on the scan-converted 3D data to be fitted in the selected display layout.

6. A method for displaying a target object by using 3D ultrasound data, comprising the steps of:
   storing indices of 3D data matched with Cartesian coordinates of a screen in a display device to display a 3D image of the target object and resulting values of operations to convert Cartesian coordinates to conical coordinates in a geometric look-up table storage unit;
   receiving information of a reference sectional plane from an interface device, receiving 3D data of the target object from a probe or a 3D data storage device, and determining whether a current display region displaying an ultrasound image based on the 3D data of the target object is different from a previous display region on the screen;
   calculating the display region to display the image on the screen when the display region is changed;
   scan-converting 3D data of the target object by retrieving the resulting values from the geometric look-up table storage unit in order to convert the Cartesian coordinates corresponding to the calculated display region to the conical coordinates of the 3D data of the target object; and
   rendering multiple sectional plane images based on the scan-converted 3D data, wherein the multiple sectional plane images are parallel with a reference sectional plane in a vertical direction to the reference sectional plane.

7. The method as recited in claim 6, further comprising the steps of:
   drawing a line on the reference sectional plane for displaying a desired sectional plane; and
   displaying the desired sectional plane perpendicular to the reference sectional plane taken along the line by using an anti-aliasing method.

8. The method as recited in claim 6, further comprising the step of moving or editing an image displayed on the screen.

9. The method as recited in claim 6, wherein the multiple sectional plane images are displayed in real time in an ultrasound diagnostic device.

10. The method as recited in claim 6, wherein a desired display layout for displaying the multiple sectional plane images is selected through the interface device, and wherein the rendering step is performed by rendering the multiple sectional plane images based on the scan-converted 3D data to be fitted in the selected display layout.

11. The method as recited in claim 7, wherein the anti-aliasing method is a selective anti-aliasing method for retrieving an aliased portion and performing the anti-aliasing method only for the aliased portion.

12. A method for displaying slice images of a target object by using 3D ultrasound data, comprising the steps of:
   setting a reference sectional plane of the target object to be displayed;
   acquiring the 3D ultrasound data of the target object;
   generating and displaying the reference sectional plane image based on the 3D ultrasound data;
   drawing a line on the displayed reference sectional plane for displaying a desired sectional plane; and
   generating and displaying the desired sectional plane perpendicular to the reference sectional plane taken along the line by using a selective anti-aliasing method for retrieving an aliased portion by using a slope of the drawn line and for performing the anti-aliasing method only for the aliased portion.

13. The method as recited in claim 11, wherein the 3D ultrasound data are stored in a storage medium beforehand.

* * * * *